(12) United States Patent
Shimizu

(10) Patent No.: US 11,199,556 B2
(45) Date of Patent: Dec. 14, 2021

(54) MEASURING APPARATUS, COMPUTER READABLE MEDIUM STORING MEASURING PROGRAM AND MEASURING METHOD

(71) Applicant: ARKRAY, Inc., Kyoto (JP)

(72) Inventor: Takeshi Shimizu, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 749 days.

(21) Appl. No.: 16/025,514

(22) Filed: Jul. 2, 2018

(65) Prior Publication Data
US 2019/0011467 A1 Jan. 10, 2019

(30) Foreign Application Priority Data

Jul. 4, 2017 (JP) .............................. JP2017-131326
Jun. 28, 2018 (JP) .............................. JP2018-123619

(51) Int. Cl.
*G01N 35/00* (2006.01)
*A61B 5/145* (2006.01)
(Continued)

(52) U.S. Cl.
CPC ......... *G01N 35/00693* (2013.01); *A61B 5/01* (2013.01); *A61B 5/0205* (2013.01);
(Continued)

(58) Field of Classification Search
CPC ....... G01N 35/00693; G01N 33/48785; G01N 33/49; G01N 2035/00702; G01N 27/26;
(Continued)

(56) References Cited

U.S. PATENT DOCUMENTS

2009/0281406 A1* 11/2009 McGarraugh ........ A61B 5/1486
600/365
2009/0299155 A1* 12/2009 Yang ................ A61B 5/150389
600/301
(Continued)

FOREIGN PATENT DOCUMENTS

JP 2011-062335 A1 3/2011

OTHER PUBLICATIONS

Extended European Search Report issued in corresponding European Patent Application No. 18181510.1 dated Dec. 3, 2018.

*Primary Examiner* — Omar Casillashernandez
(74) *Attorney, Agent, or Firm* — Morgan, Lewis & Bockius LLP

(57) ABSTRACT

A measuring apparatus includes: a measuring unit to measure a signal value corresponding to a concentration of a specified substance of a first sample; an acquiring unit to acquire a reference value pertaining to the specified substance of a second sample; a calculating unit to calculate a concentration value of the specified substance of the first sample, based on the signal value and the reference value; a timing determination unit to determine timing for calibrating the reference value when satisfying at least one of a first condition that an activity status of a user is a predetermined status and a second condition that a variation in the concentration value of the specified substance of the first sample is equal to or smaller than a threshold value; and an input request unit to request the user to input the reference value at the determined timing.

15 Claims, 5 Drawing Sheets

(51) Int. Cl.
*A61B 5/1495* (2006.01)
*A61B 5/00* (2006.01)
*A61B 5/01* (2006.01)
*A61B 5/0205* (2006.01)
*A61B 5/11* (2006.01)
*G01N 33/487* (2006.01)
*G01N 33/49* (2006.01)
*A61B 5/021* (2006.01)
*A61B 5/024* (2006.01)
*A61B 5/15* (2006.01)
*A61B 10/00* (2006.01)

(52) U.S. Cl.
CPC .......... *A61B 5/1118* (2013.01); *A61B 5/1451* (2013.01); *A61B 5/1495* (2013.01); *A61B 5/14532* (2013.01); *A61B 5/4839* (2013.01); *G01N 33/48785* (2013.01); *G01N 33/49* (2013.01); *A61B 5/021* (2013.01); *A61B 5/024* (2013.01); *A61B 5/15* (2013.01); *A61B 2010/008* (2013.01); *A61B 2560/0223* (2013.01); *G01N 2035/00702* (2013.01)

(58) Field of Classification Search
CPC ............ G01N 27/3271; G01N 27/3272; A61B 5/1451; A61B 5/1495; A61B 5/4839; A61B 5/14532; A61B 5/01; A61B 5/0205; A61B 5/1118; A61B 2560/0223; A61B 5/021; A61B 5/024; A61B 5/15; A61B 2010/008
USPC .......................................................... 702/19
See application file for complete search history.

(56) References Cited

U.S. PATENT DOCUMENTS

| | | | |
|---|---|---|---|
| 2011/0029269 A1* | 2/2011 | Hayter | A61M 5/1723 |
| | | | 702/104 |
| 2014/0171771 A1* | 6/2014 | Feldman | A61B 5/1451 |
| | | | 600/345 |
| 2015/0190098 A1* | 7/2015 | Patek | A61B 5/486 |
| | | | 600/365 |
| 2016/0007934 A1* | 1/2016 | Arnold | A61B 5/681 |
| | | | 600/595 |
| 2016/0062570 A1* | 3/2016 | Dascola | H04W 68/00 |
| | | | 715/765 |
| 2017/0045622 A1* | 2/2017 | Matsumoto | A61B 5/1112 |
| 2018/0303389 A1* | 10/2018 | Sloan | G16H 20/17 |
| 2018/0344178 A1* | 12/2018 | Deng | A61B 5/0205 |
| 2021/0146117 A1* | 5/2021 | Reich | G16H 50/50 |

* cited by examiner

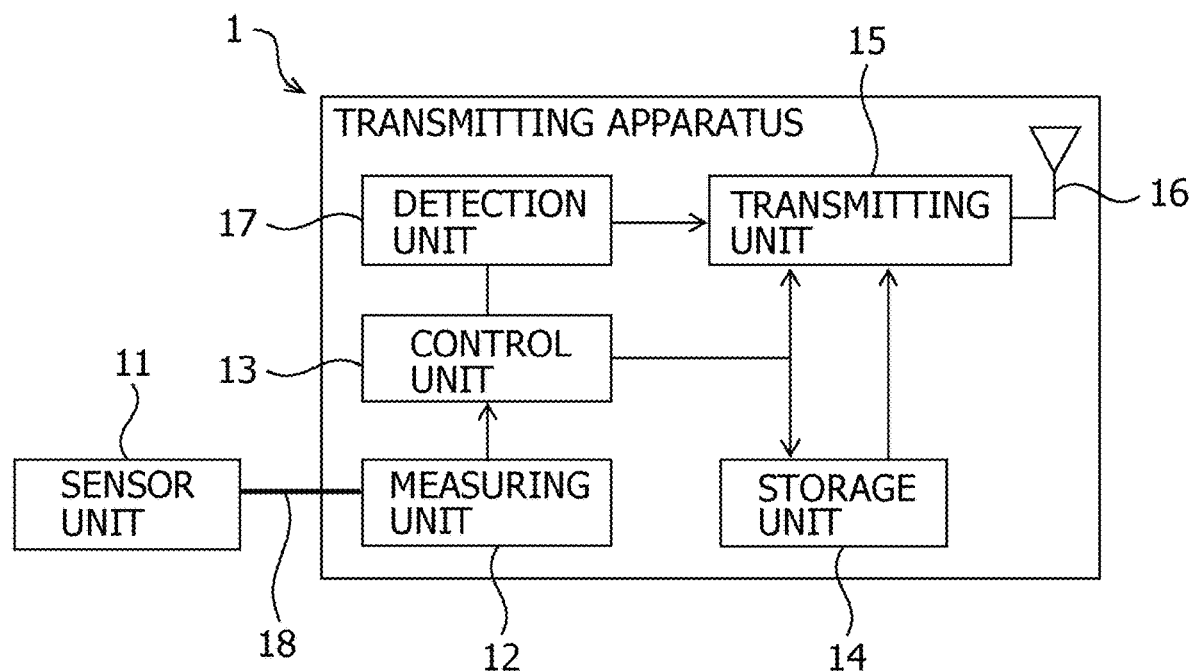
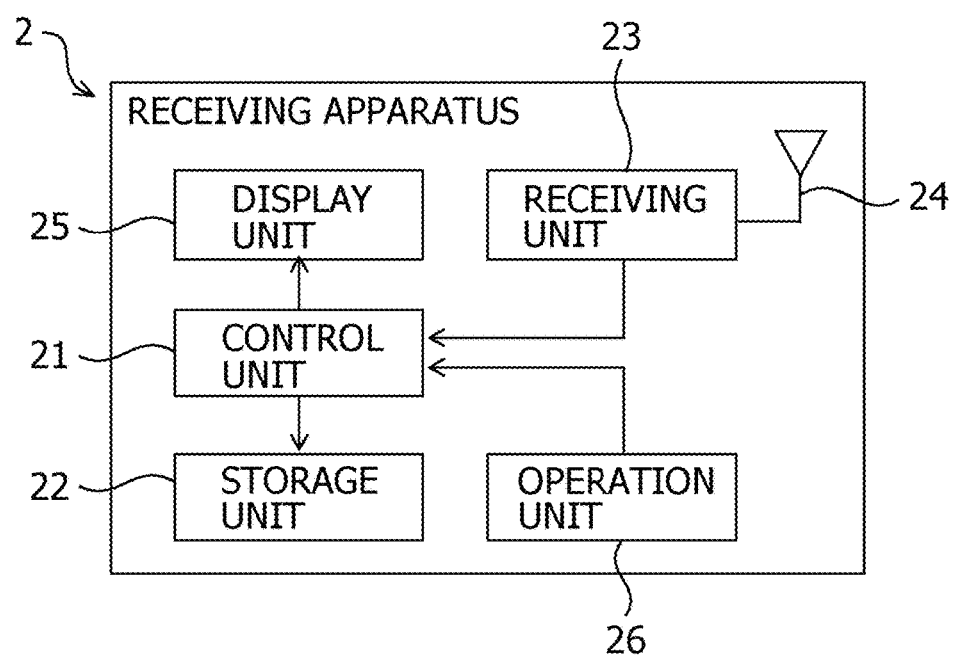

MEASURING APPARATUS, COMPUTER READABLE MEDIUM STORING MEASURING PROGRAM AND MEASURING METHOD

CROSS-REFERENCE TO RELATED APPLICATION

The present application claims priority to Japanese Patent Application No. 2017-131326, filed Jul. 4, 2017, and Japanese Patent Application No. 2018-123619, filed Jun. 28, 2018, the entire contents of which are incorporated herein by reference.

FIELD

An embodiment pertains to a measuring apparatus, a measuring program and a measuring method.

BACKGROUND

A variety of blood glucose level measuring apparatuses for measuring a self blood glucose level (a glucose concentration value in blood) are currently put on sale in the market. Known as the blood glucose level measuring apparatus are, e.g., a Self-Monitoring of Blood Glucose (SMBG) apparatus for self-monitoring (measuring) of the blood glucose and a Continuous Glucose Monitoring (CGM) apparatus for continuous glucose monitoring (measuring). The SMBG apparatus measures the blood glucose level in a way that attaches blood extracted from a finger tip by using a needling tool onto a test piece fitted to measurement equipment. The CGM apparatus continuously measures a glucose concentration in interstitial fluid by subcutaneously indwelling a micro sensor including electrodes and enzyme reacting to the glucose. The CGM apparatus consecutively measures the blood glucose level at an interval of several tens of seconds through several minutes by subcutaneously indwelling the sensor over a period as long as several days through several weeks.

There exists a divergence between the blood glucose level and the glucose concentration value in the interstitial fluid. Therefore, the CGM apparatus corrects the glucose concentration value in the interstitial fluid with reference to the inputted blood glucose level, and gets the glucose concentration value in the interstitial fluid approximate to the blood glucose level. The CGM apparatus calibrates the CGM by inputting the blood glucose level at an interval of fixed period. A calibration cycle of the CGM depends on performance of a sensor of the CGM apparatus, and is exemplified by four times/day, twice/day and once/day. For example, when the calibration cycle of the CGM is twice/day, a request for inputting the blood glucose level is automatically made after 11-12 hours since the blood glucose level has been inputted last time. Known is a blood glucose level monitoring apparatus that automatically calibrates an estimation blood glucose level, which is estimated non-invasively, by using an invasively-measured reference blood glucose level (e.g., Patent document 1).

[Patent document 1] Japanese Laid-open Patent Publication No. 2011-62335

SUMMARY

The calibration of the CGM involves using the blood glucose level measured by the SMBG apparatus, and a time lag, however, exists between the blood glucose level and the glucose concentration value in the interstitial fluid, which is defined as a CGM measuring target value. In other words, a fixed period of time is taken till the glucose concentration value in the interstitial fluid follows up the blood glucose level. Hence, the CGM calibration being made when there is a large variation in blood glucose level adversely affects accuracy of a measurement value of the CGM apparatus due to influence of the time lag.

However, in a conventional technology, the request for inputting the blood glucose level is automatically made after 11-12 hours since the blood glucose level has been inputted last time without taking account of whether the variation in blood glucose level is large when the CGM calibration cycle is, e.g., twice/day. Further, in the conventional technology, the request for inputting the blood glucose level is automatically made after 11-12 hours since the blood glucose level has been inputted last time without taking account of an activity status of the user (e.g., a status of the user being kept in sleep) when the CGM calibration cycle is, e.g., twice/day. When the request for inputting the blood glucose level is automatically made in the status of the user being kept in sleep, such a problem arises as to give a burden to the user. The present invention is devised in view of such actual circumstances, and aims at improving accuracy of a measurement value of a concentration of a specified substance in a sample, and relieving the burden on the user in the measurement of the concentration of the specified substance in the sample.

According to an aspect of the embodiment, a measuring apparatus includes: a status determining unit configured to determine an activity status of a user from a signal outputted by at least one activity sensor configured to detect an activity factor of the user; a measuring unit configured to measure a signal value corresponding to a concentration of a specified substance contained in a first sample; an acquiring unit configured to acquire a reference value pertaining to the specified substance contained in a second sample; a calculating unit configured to calculate a concentration value of the specified substance contained in the first sample, based on the signal value and the reference value; a timing determination unit configured to determine timing for calibrating the reference value when satisfying at least one of a first condition that the activity status of the user is a predetermined status and a second condition that a variation in the concentration value of the specified substance contained in the first sample is equal to or smaller than a threshold value; and an input request unit configured to request the user to input the reference value at the determined timing.

According to the embodiment, it is feasible to improve the accuracy of the measurement value of the concentration of the specified substance in the sample, and to relieve the burden on the user in the measurement of the concentration of the specified substance in the sample.

BRIEF DESCRIPTION OF DRAWINGS

FIG. 2 is a block diagram of a configuration of a transmitting apparatus according to the embodiment;

FIG. 3 is a block diagram of a configuration of a receiving apparatus according to the embodiment;

DESCRIPTION OF EMBODIMENT

Figure 1:
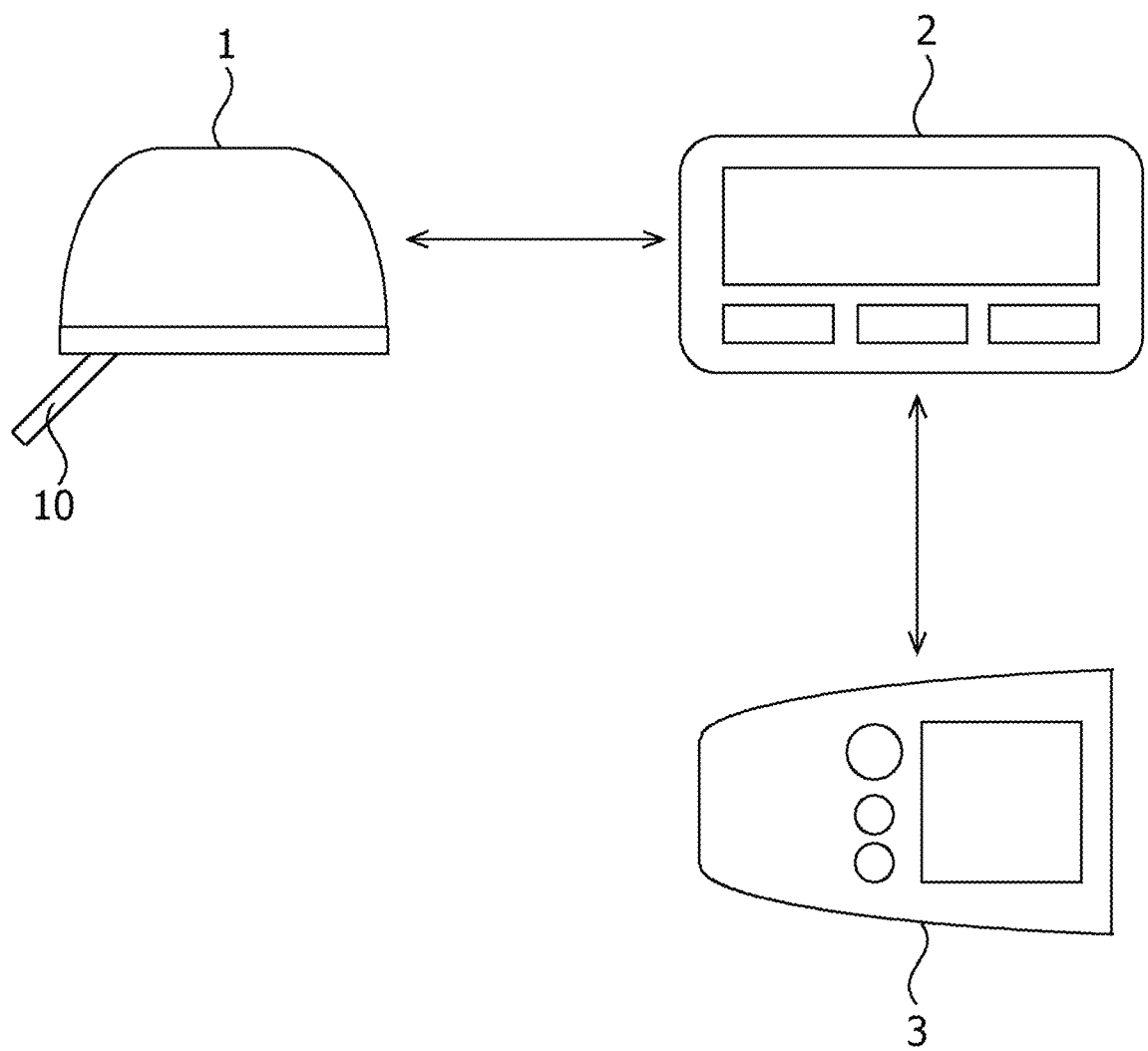
FIG. 1 is a diagram of a configuration of a measuring system according to an embodiment.

An embodiment will hereinafter be described with reference to the drawings. The following embodiment is an exemplification, and the present invention is not limited to a configuration of the embodiment given below.

According to an embodiment, the timing for calibrating the reference value is determined when satisfying at least one of the first condition that the activity status of the user is the predetermined status and the second condition that the variation in the concentration value of the specified substance contained in the first sample is equal to or smaller than the threshold value. The user is requested to input the reference value at the determined timing, and hence the burden and a sense of discomfort of the user are relieved. According to the embodiment, when the variation in the concentration value of the specified substance contained in the first sample is equal to or smaller than the threshold value, the timing for calibrating the reference value is determined. Improved therefore are the accuracy of the reference value pertaining to the specified substance contained in the second sample and the accuracy of the concentration value of the specified substance contained in the first sample. This results in restraining the divergence between the concentration value of the specified substance contained in the first sample and the concentration value of the specified substance contained in the second sample.

The measuring apparatus further includes: a calibrating unit to calibrate the reference value, wherein the timing determination unit determines the timing when satisfying a condition that elapse time since calibrating the reference value is equal to or longer than predetermined time and at least one of the first condition and the second condition. In the measuring apparatus, the at least one activity sensor includes a motion sensor configured to detect a motion quantity of the user, and the status determining unit determines the activity status of the user, based on the motion quantity of the user. In the measuring apparatus, the at least one activity sensor includes an attitude sensor configured to detect an attitude of the user, and the status determining unit determines the activity status of the user, based on the attitude of the user.

In the measuring apparatus, the at least one activity sensor includes a temperature sensor configured to detect a body temperature of the user, and the status determining unit determines the activity status of the user, based on the body temperature of the user. In the measuring apparatus, the at least one activity sensor includes a pulse sensor configured to measure a pulse rate of the user, a heartbeat sensor configured to measure a heart rate of the user, or a pulse wave sensor configured to measure a pulse wave of the user, and the status determining unit determines the activity status of the user, based on the pulse rate of the user, the heart rate of the user, or the pulse wave of the user. In the measuring apparatus, the at least one activity sensor includes a blood pressure sensor configured to measure a blood pressure value of the user, and the status determining unit determines the activity status of the user, based on the blood pressure value of the user. In the measuring apparatus, the first sample is interstitial fluid, the second sample is blood, and the specified substance is glucose.

The aspect described above may be attained in a way that causes a program to be run by a computer. To be specific, the aspect described above may be specified as a program to be run by the computer, or as a computer readable recording medium on which the program is recorded. The aspect described above may also be specified as a method executed by the computer. The aspect described above may further be specified as a system including the measuring apparatus.

FIG. 1 is a diagram of a configuration of a measuring system according to the embodiment. The measuring system illustrated in FIG. 1 includes a transmitting apparatus 1, a receiving apparatus 2 and a detection apparatus 3. The transmitting apparatus 1 consecutively measures a concentration of a specified substance (measurement target substance) in a first sample in vivo, and transmits a measurement result to the receiving apparatus 2. The transmitting apparatus 1 may be used by being attached to regions instanced by an abdominal region and a shoulder of a user (patient). The transmitting apparatus 1 may also be a Continuous Glucose Monitoring (CGM) apparatus for performing continuous glucose monitoring (measurement). A body fluid instanced by an interstitial fluid is given as the first sample in vivo. The specified substance is exemplified by glucose contained in the interstitial fluid. The specified substance may also be a substance other than glucose.

The receiving apparatus 2 receives a measurement result from the transmitting apparatus 1. The receiving apparatus 2 performs wireless data communications with the transmitting apparatus 1, and also performs the wireless data communications with the detection apparatus 3. The receiving apparatus 2 may perform wired data communications with the transmitting apparatus 1, and may also perform the wired data communications with the detection apparatus 3. The transmitting apparatus 1 and the receiving apparatus 2 are configured as separate equipments in the embodiment, and may also be configured integrally.

The detection apparatus 3 is an apparatus to measure a concentration of the specified substance in a second sample extracted in vitro. A body fluid instanced by blood is given as the second sample extracted in vitro. The detection apparatus 3 may also be a Self-Monitoring of Blood Glucose (SMBG) apparatus for conducting self-monitoring of blood glucose. The detection apparatus 3 measures a current value corresponding to a glucose concentration in the blood. The detection apparatus 3 converts the current value into a glucose concentration value in the blood with reference to calibration curve data, thereby measuring the glucose concentration value in the blood. The current value and the glucose concentration value in the blood, which are measured by the detection apparatus 3, are transmitted and inputted to the receiving apparatus 2. The detection apparatus 3 may also display the glucose concentration value in the blood on a display provided on the detection apparatus 3. The user may input the glucose concentration value in the blood, which is displayed on the display of the detection apparatus 3, to the receiving apparatus 2.

<Transmitting Apparatus>

The transmitting apparatus 1 includes a measurement sensor 10 is used by being implanted into a subcutaneous region of the user. The transmitting apparatus 1 is pasted to a skin of the user by an adhesive tape and other equivalent materials, or is attached to a belt and other equivalent articles, thereby being fitted to the user. The measurement sensor 10 is an electrochemical sensor that measures a specified component (e.g., a concentration of the specified substance) in the first sample by utilizing electrochemical reaction. The measurement sensor 10 is indwelled subcutaneously over a consecutive measurement period as long as, e.g., several days through several weeks, and the transmitting apparatus 1 consecutively measures the glucose concentration in the interstitial fluid. "Being consecutive" connotes that the transmitting apparatus 1 continuously measures the glucose concentration in a state of the measurement sensor 10 being subcutaneously indwelled, and encompasses such a mode that the transmitting apparatus 1 measures the glucose concentration at an interval of predetermined time. A measurement frequency of the glucose concentration may be arbitrarily set with respect to the transmitting apparatus 1. For example, the measurement frequency of the glucose concentration may also be set with respect to the transmitting apparatus 1 so that the transmitting apparatus 1 measures the glucose concentration at a frequency of once every several ten seconds through several minutes.

FIG. 2 is a block diagram of a configuration of the transmitting apparatus 1 according to the embodiment. The transmitting apparatus 1 is a transmitter that transmits various items of data to the receiving apparatus 2. The transmitting apparatus 1 includes a sensor unit 11, a measurement unit 12, a control unit (arithmetic unit) 13, a storage unit 14, a transmitting unit 15, an antenna 16, and a detection unit 17. The sensor unit 11 has glucose oxidoreductase instanced by glucose oxidase (GOD) and glucose dehydrogenase (GDH), and a plurality of electrodes, i.e., a working electrode, a counter electrode, a reference electrode and other equivalent electrodes. The sensor unit 11 is provided on the side of a tip of the measurement sensor 10 illustrated in FIG. 1. The sensor unit 11 is electrically connected to the measurement unit 12 via a wire 18.

The measurement unit 12 is a circuit to measure a signal value (e.g., a response current value) by applying a voltage to the sensor unit 11. When the voltage is applied to between the electrodes (between the working electrode and the counter electrode, or between the working electrode and the reference electrode) of the sensor unit 11, the sensor unit 11 outputs a response current value corresponding to the glucose concentration in the body fluid. The measurement unit 12 measures the response current value outputted from the sensor unit 11 in a way that controls the voltage to be applied to between the electrodes of the sensor unit 11. When the voltage is applied to between the electrodes of the sensor unit 11, the glucose in the body fluid is oxidized by the oxidoreductase, and electrons being thereby extracted are supplied to the working electrode. The measurement unit 12 measures, as the response current value, a quantity of electric charges of the electrons supplied to the working electrode. The measurement unit 12 may convert the response current value into a response voltage value, and may measure, as the response voltage value, the quantity of electric charges of the electrons supplied to the working electrode. The following discussion will deal with a case that the measurement unit 12 measures the response current value. The response current value measured by the measurement unit 12 is sent to the control unit 13.

The control unit 13 controls the measurement unit 12, the storage unit 14, the transmitting unit 15, and the detection unit 17. The control unit 13, the storage unit 14 and the transmitting unit 15 may be attained by: computers each including a Central Processing Unit (CPU), a Random Access Memory (RAM), a Read Only Memory (ROM) and other equivalent hardware components that are provided in the transmitting apparatus 1; respective apparatuses; and programs and other equivalent software components running on the computer. The CPU is also called a processor. It does not mean that the CPU is limited to the single processor, and the CPU may, however, take a multi-processor configuration.

The control unit 13 stores the response current value in the storage unit 14, and sends the response current value to the transmitting unit 15. The transmitting unit 15 transmits the response current value to the receiving apparatus 2 via the antenna 16. The transmitting unit 15 may send the response current value transmitted from the control unit 13 to the receiving apparatus 2, and may also send the response current value stored in the storage unit 14 to the receiving apparatus 2.

The detection unit 17 detects an activity factor of the user attached with the transmitting apparatus 1, and outputs a signal corresponding to the activity factor of the user. The detection unit 17 has at least one of a motion sensor, an attitude sensor and a vital sensor. The motion sensor is an activity sensor to detect a quantity of motion of the user attached with the transmitting apparatus 1, and, e.g., an acceleration sensor is given as the motion sensor. The attitude sensor is an activity sensor to detect an attitude of the user attached with the transmitting apparatus 1, and, e.g., a gyro sensor is given as the attitude sensor. The vital sensor is an activity sensor to measure vital data of the user attached with the transmitting apparatus 1, and, e.g., each of a temperature sensor, a pulse sensor, a heartbeat sensor, a pulse wave sensor and a blood pressure sensor is given as the vital sensor. The temperature sensor measures a body temperature of the user attached with the transmitting apparatus 1. The pulse sensor measures a pulse rate of the user attached with the transmitting apparatus 1. The heartbeat sensor measures a heart rate (heartbeat rate) of the user attached with the transmitting apparatus 1. The pulse wave sensor measures pulse waves of the user attached with the transmitting apparatus 1. The blood pressure sensor measures a blood pressure level of the user attached with the transmitting apparatus 1.

The user's activity factor detected by the detection unit 17 is sent as activity factor data to the transmitting unit 15. The transmitting unit 15 transmits the activity factor data to the receiving apparatus 2 via the antenna 16. The activity factor data includes at least one of motion quantity data (acceleration data), attitude data (angular velocity data and angular acceleration data), body temperature data, pulse rate data, heart rate data, pulse wave data and blood pressure level data. The activity factor data is one example of "signal".

<Receiving Apparatus>

FIG. 3 is a block diagram illustrating a configuration of the receiving apparatus 2 according to the embodiment. The receiving apparatus 2 receives the various items of data from the transmitting apparatus 1, and displays the received data. The receiving apparatus 2 includes a control unit (arithmetic unit) 21, a storage unit 22, a receiving unit 23, an antenna 24, a display unit 25, and an operation unit 26. The control unit 21 controls the storage unit 22, the receiving unit 23, and the display unit 25. The control unit 21, the storage unit 22, and the receiving unit 23 may be attained by: computers each including the CPU, the RAM, the ROM and other equivalent hardware components that are provided in the receiving apparatus 2; respective apparatuses; and programs and other equivalent software components running on the computer.

The display unit 25 has a display and displays various types of information and messages on this display. The display unit 25 displays a measurement result and an error on the display, and also displays operation procedures, operation statuses and other equivalent items when setting is done. The display of the display unit 25 is exemplified by a liquid crystal display apparatus, a plasma display panel, a Cathode Ray Tube (CRT) display, or an Electroluminescence (EL) panel. The display unit 25 may have a voice output unit to output voices and sounds. The operation unit 26 includes a variety of operation buttons, a touch panel and other equivalent components, and accepts the various types of information from the user.

The receiving unit 23 receives the response current value and the activity factor data from the transmitting apparatus 1 via the antenna 24, and sends the received response current value and the activity factor data to the control unit 21. The control unit 21 stores the received response current value and the activity factor data in the storage unit 22. The control unit 21 converts the response current value into the glucose concentration value with reference to calibration curve data stored in the storage unit 22. The calibration curve data indicating a correspondence relation between the response current value and the glucose concentration in the interstitial fluid is pre-stored in the storage unit 22. The calibration curve data is pre-stored as, e.g., a mathematical expression and a correspondence table in the storage unit 22. The control unit 21 is one example of a "measuring unit".

The control unit 21 determines an activity status of the user from the activity factor data. The control unit 21 is one example of a "status determining unit". The control unit 21 calculates an activity quantity of the user from the motion quantity data. For example, the control unit 21 may calculate a number of steps per unit time from the motion quantity data, and may calculate the number of steps per unit time as the user's activity quantity. The user's motion quantity tends to be large when the user is kept in motion, and tends to be small when the user is kept in rest. The control unit 21 may calculate the user's activity quantity from the motion quantity data and the attitude data. The control unit 21 determines, when the user's activity quantity falls within a range of predetermined quantity, that an activity status of the user is defined as a first status. A status of the user not being kept in motion (non-motion status) is given as one example of the first status.

The control unit 21 calculates a user's attitude from the attitude data. The control unit 21 may calculate the user's attitude from the motion quantity data and the attitude data. The control unit 21 determines, when the user's attitude is a predetermined attitude, that the activity status of the user is defined as a second status. For example, a status of the user standing and a status of the user sitting are each given as one example of the second status. The control unit 21 may digitize the user's attitude, and may calculate a digitized value as the user's activity quantity. For instance, the control unit 21 may calculate the status of the user standing and the status of the user sitting as "0", and may calculate a status of the user lying as "1". The control unit 21 determines, when the user's activity quantity falls within the range of predetermined quantity, that the user's activity is defined as the second status.

The control unit 21 calculates a body temperature (temperature value) of the user from the body temperature data. The control unit 21 determines, when the body temperature of the user falls within a range of predetermined temperature, that the user's activity status is defined as a third status. The body temperature of the user tends to ascend when the user is kept in motion and in meal, and tends to descend when the user is kept in sleep. For example, a status of the user being kept in non-motion, a status of the user not being kept in meal (non-meal status) and a status of the user not being kept in sleep (non-sleep status) are each given as one example of the third status. The control unit 21 may determine, based on a user's average body temperature as a reference, whether the user's body temperature falls within a range of predetermined temperature. The control unit 21 may also calculate the user's body temperature as the user's activity quantity. The control unit 21 determines, when the user's activity quantity falls within a range of predetermined quantity, that the user's activity status is defined as the third status.

The control unit 21 calculates the user's pulse rate from the pulse rate data. The control unit 21 determines, when the user's pulse rate falls within a range of predetermined pulse rate, that the user's activity status is defined as the third status. The user's pulse rate tends to ascend when the user is kept in motion and in meal, and tends to descend when the user is kept in sleep. The control unit 21 may determine, based on the user's average pulse rate as a reference, whether the user's pulse rate falls within a range of predetermined pulse rate. The control unit 21 may also calculate the user's pulse rate as the user's activity quantity. The control unit 21 determines, when the user's activity quantity falls within a range of predetermined quantity, that the user's activity status is defined as the third status.

The control unit 21 calculates the user's heart rate from the heart rate data. The control unit 21 determines, when the user's heart rate falls within a range of predetermined heart rate, that the user's activity status is defined as the third status. The user's heart rate tends to ascend when the user is kept in motion and in meal, and tends to descend when the user is kept in sleep. The control unit 21 may determine, based on the user's average heart rate as a reference, whether the user's heart rate falls within a range of predetermined heart rate. The control unit 21 may also calculate the user's heart rate as the user's activity quantity. The control unit 21 determines, when the user's activity quantity falls within the range of predetermined quantity, that the user's activity status is defined as the third status.

The control unit 21 calculates a waveform of the user's pulse wave from the pulse wave data. The control unit 21 may compare the waveform of the user's pulse wave with a waveform of a predetermined pulse wave that is pre-stored in the storage unit 22, and may determine whether the user's activity status is defined as the third status. The waveform of the predetermined pulse wave may also be stored in the storage unit 22. The control unit 21 may calculate the user's pulse rate by making a frequency analysis about the waveform of the user's pulse wave.

The control unit 21 calculates a user's blood pressure level from the blood pressure level data. The control unit 21 determines, when the user's blood pressure level falls within a range of predetermined level, that the user's activity status is defined as the third status. The user's blood pressure level tends to ascend when the user is kept in motion and in meal, and tends to descend when the user is kept in sleep. The control unit 21 may determine, based on an average blood pressure level of the user as a reference, whether the user's blood pressure level falls within the range of predetermined level. The control unit 21 may also calculate the user's blood pressure level as the user's activity quantity. The control unit 21 determines, when the user's activity quantity falls within the range of predetermined quantity, that the user's activity status is defined as the third status.

The receiving unit 23 receives a reference value pertaining to the glucose in the blood (which will hereinafter be referred to as a glucose reference value) from the detection apparatus 3 via the antenna 24, and sends the received glucose reference value to the control unit 21. The control unit 21 acquires the glucose reference value and stores the glucose reference value in the storage unit 22. The control unit 21 is one example of an "acquiring unit". The control unit 21 corrects the glucose concentration value in the interstitial fluid by using the glucose reference value. The glucose concentration value in the blood is not coincident with the glucose concentration value in the interstitial fluid. Therefore, the control unit 21 corrects the glucose concentration value in the interstitial fluid by use of the glucose reference value, thereby executing a process of making the glucose concentration value in the interstitial fluid approximate to the glucose concentration value in the blood.

The glucose reference value is, e.g., the current value measured by the detection apparatus 3, or the glucose concentration value in the blood, which is measured by the detection apparatus 3. The control unit 21 may calculate the glucose concentration value in the interstitial fluid on the basis of the response current value, and may correct the glucose concentration value in the interstitial fluid with reference to the in-blood glucose concentration value (the glucose concentration value in the blood) measured by the detection apparatus 3. The glucose concentration value in the interstitial fluid, which is corrected with reference to the in-blood glucose concentration value measured by the detection apparatus 3, will hereinafter be termed a post-correction glucose concentration value. The control unit 21 may correct the response current value with reference to the current value measured by the detection apparatus 3, and may calculate the glucose concentration value in the interstitial fluid on the basis of the post-correction response current value. The glucose concentration value in the interstitial fluid, which is calculated based on the post-correction response current value, will hereinafter be termed the post-correction glucose concentration value. The control unit 21 is one example of a "calculating unit".

The control unit 21 determines timing for calibrating the glucose reference value on the basis of the user's activity status and a variation in the glucose concentration value in the interstitial fluid. The control unit 21 determines the timing for calibrating the glucose reference value when the user's activity status is the predetermined status and when the variation in the glucose concentration value in the interstitial fluid is equal to or smaller than a threshold value. The control unit 21 may determine the timing for calibrating the glucose reference value when satisfying at least one of a first condition that the user's activity status is the predetermined status and a second condition that the variation in the glucose concentration value in the interstitial fluid is equal to or smaller than the threshold value. The predetermined status encompasses the first through third statuses. The control unit 21 may determine that the variation in the glucose concentration value in the interstitial fluid is equal to or smaller than the threshold value when each of the glucose concentration values in the interstitial fluid, which are measured a plural number of times, falls within the range of predetermined concentration value. The control unit 21 may also determine the timing for calibrating the glucose reference value, based on any one of the user's activity status and the variation in the glucose concentration value in the interstitial fluid. The control unit 21 is one example of a "timing determination unit".

For example, when the user is kept in the motion status, in the meal status and in the sleep status, requesting the user to calibrate the glucose reference value gives a burden and a sense of discomfort to the user. For instance, when the user is kept in the non-motion status, in the non-meal status and in the non-sleep status, requesting the user to calibrate the glucose reference value relieves the burden and the sense of discomfort to the user.

The control unit 21 displays, based on the determined timing, a message requesting the calibration of the glucose reference value on the display unit 25. The display unit 25, when including a voice output unit, may output a voice requesting the calibration of the glucose reference value. The user measures the glucose concentration in the blood by use of the detection apparatus 3. The current value or the in-blood glucose concentration value measured by the detection apparatus 3 is sent and inputted to the receiving apparatus 2. The user may also input the glucose concentration value in the blood to the receiving apparatus 2 by operating the operation unit 26 of the receiving apparatus 2. The control unit 21 receives the in-blood glucose concentration value inputted to the receiving apparatus 2. The control unit 21 is one example of an "input request unit".

The control unit 21 updates the glucose reference value stored in the storage unit 22 on the basis of the current value or the in-blood glucose concentration value inputted to the receiving apparatus 2, thereby calibrating the glucose reference value. The control unit 21 is one example of a "calibrating unit".

There exists a time lag between the glucose concentration value in the blood and the glucose concentration value in the interstitial fluid. In other words, a fixed period of time is taken till the glucose concentration value in the interstitial fluid follows up the glucose concentration value in the blood. For example, even when there is a large variation in glucose concentration value in the interstitial fluid, a variation in the glucose concentration value in the blood is small as the case may be. Such a possibility exists that the post-correction glucose concentration value diverges largely from the glucose concentration value in the blood upon calibrating the glucose reference value when there is a large variation in the glucose concentration value in the interstitial fluid. The control unit 21 determines the timing for calibrating the glucose reference value on the basis of the variation in the glucose concentration value in the interstitial fluid, thereby restraining the divergence between the post-correction glucose concentration value and the glucose concentration value in the blood.

It is preferable that the glucose reference value is calibrated once or several times a day when taking into consideration the divergence between the glucose concentration value in the blood and the glucose concentration value in the interstitial fluid. The control unit 21 may determine the timing for calibrating the glucose reference value on the basis of the user's activity quantity and the variation in the glucose concentration value in the interstitial fluid when elapse time since calibrating the glucose reference value is equal to or longer than a predetermined period of time. Given as one example of the predetermined period of time are 24 hours, 12 hours, 8 hours and 6 hours. The user is requested to calibrate the glucose reference value after an elapse of the fixed period of time since calibrating the glucose reference value, thereby improving accuracy of the glucose reference value and relieving the burden and the sense of discomfort of the user. The improvement of the accuracy of the glucose reference value leads to an improvement of accuracy of the glucose concentration value and to a restraint on the divergence between the post-correction glucose concentration value and the glucose concentration value in the blood.

<Detection Apparatus>

Figure 4:
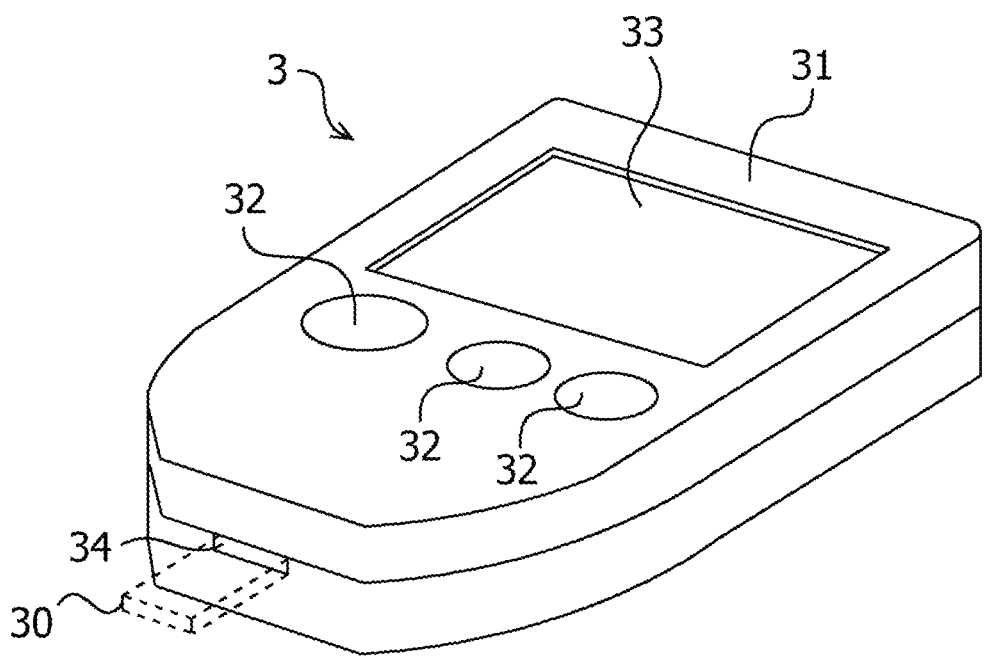
FIG. 4 is a schematic diagram illustrating a configuration of a detection apparatus according to the embodiment.

FIG. 4 is a schematic view illustrating a configuration of the detection apparatus 3 according to the embodiment. The detection apparatus 3 measures the glucose concentration in the blood by an electrochemical method using the biosensor 30. The detection apparatus 3 includes a housing 31, a plurality of operation buttons 32, a display panel 33 and a sensor insertion port 34. The detection apparatus 3 further includes, though not illustrated, a circuit board mounted with electronic components, i.e., a circuit, a CPU, a RAM, a ROM and other components that are required for predetermined operations (instanced by applying the voltage or performing communications with the outside) of the detection apparatus 3.

As depicted in FIG. 4, the housing 31 is provided with the operation buttons 32 and a display panel 33. The operation buttons 32 are employed for making various settings (setting of measurement conditions, inputting of user's ID and other equivalent settings), and for conducting operations to start and finish the measurement. The operation buttons 32 may also be a contact type touch panel. The display panel 33 displays the measurement result and the error, and further displays the operation procedures, the operation statuses and other equivalent items when setting is done. The display panel 33 is exemplified by the liquid crystal display apparatus, the plasma display panel, the CRT display, or the Electroluminescence panel. The operation buttons 32 may be integral with the display panel 33.

The biosensor 30 includes a substrate, a plurality of electrodes, i.e., the working electrode, the counter electrode and the reference electrode each provided on the substrate, and the glucose oxidoreductase. A capillary is formed inside of the biosensor 30. The capillary of the biosensor 30 is provided with a reagent layer, and retains the blood. The biosensor 30 is inserted into the sensor insertion port 34. The detection apparatus 3 applies a voltage to between the electrodes of the biosensor 30, and thus measures a signal value (e.g., the current value). When the voltage is applied to between the electrodes of the biosensor 30, the biosensor 30 outputs the response current value corresponding to the glucose concentration in the blood.

The detection apparatus 3 measures the response current value outputted from the biosensor 30 in a way that controls the voltage applied to between the electrodes of the biosensor 30. When the voltage is applied to between the electrodes of the biosensor 30, the glucose in the blood is oxidized by the glucose oxidoreductase, and the electrons being thereby extracted are supplied to the working electrode. The detection apparatus 3 measures, as the current value, the quantity of electric charges of the electrons supplied to the working electrode. The detection apparatus 3 may convert the current value into the voltage value, and may measure, as the voltage value, the quantity of electric charges of the electrons supplied to the working electrode. The embodiment will discuss a case that the detection apparatus 3 measures the current value.

Figure 5:
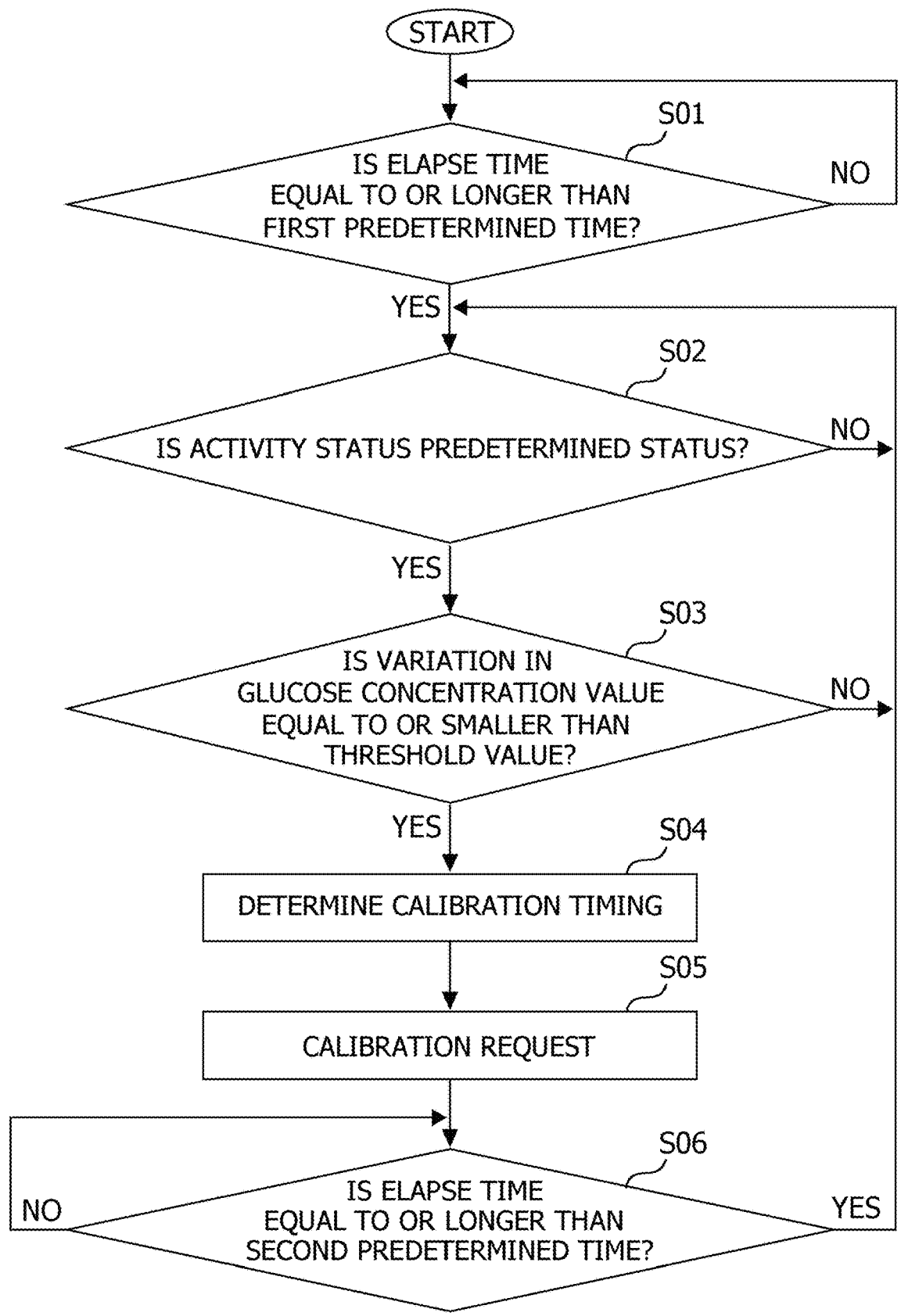
FIG. 5 is a flowchart illustrating one example of a calibration request process of a glucose reference value.

FIG. 5 is a flowchart illustrating one example of a calibration request process of the glucose reference value. Initial setting of the glucose reference value is made, which triggers a start of the flow illustrated in FIG. 5. The current value or the in-blood glucose concentration value measured by the detection apparatus 3 is inputted to the receiving apparatus 2, thereby making the initial setting of the glucose reference value. In step S01, the control unit 21 determines whether elapse time since making the initial setting of the glucose reference value is equal to or longer than first predetermined time. When the elapse time since making the initial setting of the glucose reference value is equal to or longer than the first predetermined time, the processing proceeds to step S02. Whereas when the elapse time since making the initial setting of the glucose reference value is shorter than the first predetermined time, the control unit 21 stands by till the elapse time becomes equal to or longer than the first predetermined time.

In step S02, the control unit 21 determines whether the user's activity status is the predetermined status. When the user's activity status is the predetermined status, the processing proceeds to step S03. Whereas when the user's activity status is not the predetermined status, the control unit 21 stands by till the predetermined time (e.g., 30 min) elapses, and the process in step S02 is again executed.

In step S03, the control unit 21 determines whether the variation in the glucose concentration value in the interstitial fluid is equal to or smaller than the threshold value. When the variation in the glucose concentration value in the interstitial fluid is equal to or smaller than the threshold value, the processing proceeds to step S04. Whereas when the variation in the glucose concentration value in the interstitial fluid is larger than the threshold value, the control unit 21 stands by till the predetermined time (e.g., 30 min) elapses, and the processing proceeds to step S02.

In step S04, the control unit 21 determines the timing for calibrating the glucose reference value. In step S05, the control unit 21 displays, based on the determined timing, a message requesting the calibration of the glucose reference value on the display unit 25. The display unit 25, when including the voice output unit, may output a voice requesting the calibration of the glucose reference value.

In step S06, the control unit 21 determines whether elapse time since calibrating the glucose reference value is equal to or longer than second predetermined time. When the elapse time since calibrating the glucose reference value is equal to or longer than the second predetermined time, the processing proceeds to step S02. Whereas when the elapse time since calibrating the glucose reference value is shorter than the second predetermined time, the control unit 21 stands by till the elapse time becomes equal to or longer than the second predetermined time. The second predetermined time may take the same value as the first predetermined time, and the first predetermined time and the second predetermined time may also take different values.

In the calibration request process of the glucose reference value illustrated in FIG. 5, when elapse time since making the initial setting of the glucose reference value is equal to or longer than the first predetermined time (step S01: YES), the processing may proceed to step S03. Further in the calibration request process of the glucose reference value illustrated in FIG. 5, when the user's activity status is the predetermined status (step S02: YES), the processing may proceed to step S04. Still further in the calibration request process of the glucose reference value illustrated in FIG. 5, when step S02 and step S03 may be replaced with each other. In other words, the control unit 21 may determine whether the user's activity status is the predetermined status, after determining whether the variation in the glucose concentration value in the interstitial fluid is equal to or smaller than the threshold value.

Figure 6:
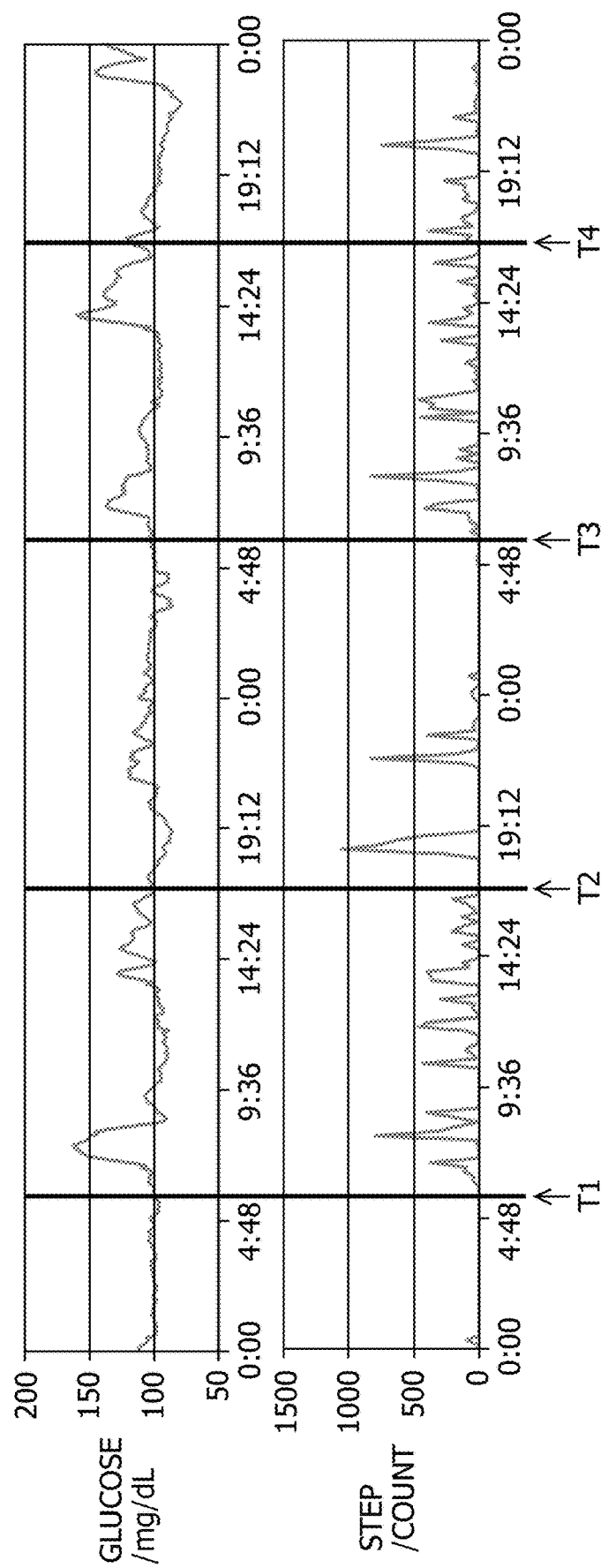
FIG. 6 is a graphic chart illustrating one example of timing for calibrating the glucose reference value.

FIG. 6 is a graphic chart illustrating one example of the timing for calibrating the glucose reference value. An upper graph in FIG. 6 indicates the variation in the glucose concentration value in the interstitial fluid together with time. A lower graph in FIG. 6 indicates the user's activity quantity together with the time. The user's activity quantity indicated by the lower graph in FIG. 6 is a number of steps per unit time. The number of steps of the user may be calculated from the acceleration data detected by the acceleration sensor. A small variation in the glucose concentration value in the interstitial fluid and a small user's activity quantity are seen at timings T1-T4 illustrated in FIG. 6. At the timings T1-T4 illustrated in FIG. 6, the user is requested to calibrate the glucose reference value, thereby improving the accuracy of the post-correction glucose concentration value and relieving the burden and the sense of discomfort of the user.

The discussion has been made above by exemplifying the measuring system including the transmitting apparatus 1, the receiving apparatus 2 and the detection apparatus 3, and the embodiment is not, however, limited to this configuration. The measuring system may include a measuring apparatus integral with the transmitting apparatus 1 and the receiving apparatus 2. The measuring system may include an analyzing apparatus including the transmitting apparatus 1, the receiving apparatus 2 and the detection apparatus 3. The control unit 13 of the transmitting apparatus 1 may also function as at least one of the "status determining unit", the "measuring unit", the "acquiring unit", the "calculating unit", the "timing determination unit", the "input request unit" and the "calibrating unit".

<Computer Readable Recording Medium>

It is possible to record a program which causes a computer, machine, system (hereinafter, described as computer and other equivalent hardware components) to implement any of the functions described above on a computer readable recording medium. By causing the computer and other equivalent hardware components to read in the program from the recording medium and execute it, the function thereof can be provided. The computer readable recording medium mentioned herein indicates a recording medium which stores information such as data and a program by an electric, magnetic, optical, mechanical, or chemical operation and allows the stored information to be read from the computer and other equivalent hardware components. Of such recording media, those detachable from the computer or the like include, e.g., a flexible disk, a magneto-optical disk, a CD-ROM, a CD-R/W, a DVD, a Blu-ray disc, a DAT, an 8-mm tape, a flash memory and a memory card. Of such recording media, those fixed to the computer and other equivalent hardware components include a hard disk, a ROM or the like.

What is claimed is:

1. A measuring apparatus comprising:
   a processor;
   a status determining unit configured to determine, using the processor, an activity status of a user from a signal outputted by at least one of a motion sensor attached to the user configured to detect a motion quantity of the user or an attitude sensor attached to the user and configured to detect an attitude of the user;
   a measuring unit configured to measure, using the processor, a signal value corresponding to a concentration of a specified substance contained in a first sample;
   an acquiring unit configured to acquire, using the processor, a reference value pertaining to the specified substance contained in a second sample;
   a calculating unit configured to calculate, using the processor, a concentration value of the specified substance contained in the first sample, based on the signal value and the reference value;
   a timing determination unit configured to determine, using the processor, timing for calibrating the reference value responsive to satisfying both a first condition that the activity status of the user is a predetermined status and a second condition that a variation in the concentration value of the specified substance contained in the first sample is equal to or smaller than a threshold value; and
   an input request unit configured to request, using the processor, the user to input the reference value to the acquiring unit at the timing determined by the timing determination unit.

2. The measuring apparatus according to claim 1, further comprising:
   a calibrating unit configured to calibrate, using the processor, the reference value, wherein the timing determination unit is configured to determine the timing responsive to satisfying a condition that elapsed time since calibrating the reference value is equal to or longer than a predetermined time and satisfying both the first condition and the second condition.

3. The measuring apparatus according to claim 1, wherein the status determining unit is configured to further determine the activity status of the user based on a signal outputted by a temperature sensor attached to the user configured to detect a body temperature of the user.

4. The measuring apparatus according to claim 1, wherein the status determining unit is configured to further determine the activity status of the user based on a signal outputted by at least one of a pulse sensor attached to the user configured to measure a pulse rate of the user, a heartbeat sensor attached to the user configured to measure a heart rate of the user, or a pulse wave sensor attached to the user configured to measure a pulse wave of the user.

5. The measuring apparatus according to claim 1, wherein the at least one activity sensor includes a blood pressure sensor configured to measure a blood pressure value of the user, and the status determining unit is configured to further determine the activity status of the user based on a signal outputted by a blood pressure sensor attached to the user configured to measure a blood pressure value of the user.

6. The measuring apparatus according to claim 1, wherein the first sample is interstitial fluid and the second sample is blood.

7. A non-transitory computer-readable medium storing a measuring program for causing a computer to execute:
   a process of determining an activity status of a user from a signal outputted by at least one of a motion sensor attached to the user configured to detect a motion quantity of the user or an attitude sensor attached to the user and configured to detect an attitude of the user;
   a process of measuring a signal value corresponding to a concentration of a specified substance contained in a first sample;
   a process of acquiring a reference value pertaining to the specified substance contained in a second sample;
   a process of calculating a concentration value of the specified substance contained in the first sample, based on the signal value and the reference value;
   a process of determining timing for calibrating the reference value responsive to satisfying both a first condition that the activity status of the user is a predetermined status and a second condition that a variation in the concentration value of the specified substance contained in the first sample is equal to or smaller than a threshold value; and
   a process of requesting the user to input the reference value to the process of acquiring at the timing determined by the process of determining timing.

8. A measuring method comprising:
   a process of determining an activity status of a user from a signal outputted by at least one of a motion sensor attached to the user configured to detect a motion quantity of the user or an attitude sensor attached to the user and configured to detect an attitude of the user;

a process of measuring a signal value corresponding to a concentration of a specified substance contained in a first sample;

a process of acquiring a reference value pertaining to the specified substance contained in a second sample;

a process of calculating a concentration value of the specified substance contained in the first sample, based on the signal value and the reference value;

a process of determining timing for calibrating the reference value responsive to satisfying both a first condition that the activity status of the user is a predetermined status and a second condition that a variation in the concentration value of the specified substance contained in the first sample is equal to or smaller than a threshold value; and a process of requesting the user to input the reference value to the process of acquiring at the timing determined by the process of determining timing.

9. The measuring apparatus according to claim 6, wherein the specified substance is glucose.

10. The non-transitory computer-readable medium according to claim 7 storing the measuring program for further causing the computer to execute:

a process of calibrating the reference value, wherein the process of determining the timing includes determining the timing responsive to satisfying a condition that elapsed time since calibrating the reference value is equal to or longer than a predetermined time and satisfying both the first condition and the second condition.

11. The non-transitory computer-readable medium according to claim 7, wherein the first sample is interstitial fluid and the second sample is blood.

12. The non-transitory computer-readable medium according to claim 11, wherein the specified substance is glucose.

13. The measuring method according to claim 8, further comprising:

a process of calibrating the reference value, wherein the process of determining the timing includes determining the timing responsive to satisfying a condition that elapsed time since calibrating the reference value is equal to or longer than a predetermined time and satisfying both the first condition and the second condition.

14. The measuring method according to claim 8, wherein the first sample is interstitial fluid and the second sample is blood.

15. The measuring method according to claim 14, wherein the specified substance is glucose.

* * * * *